United States Patent [19]
Nemesdy et al.

[11] Patent Number: 5,497,787
[45] Date of Patent: Mar. 12, 1996

[54] LIMB MONITORING METHOD AND ASSOCIATED APPARATUS

[76] Inventors: Gabor Nemesdy, 200 E. 16th St., Apt. 20A, New York, N.Y. 10003; Peter J. Wilk, 185 W. End Ave., New York, N.Y. 10023

[21] Appl. No.: 286,684

[22] Filed: Aug. 5, 1994

[51] Int. Cl.$^6$ .................................................. A61B 5/103
[52] U.S. Cl. .................... 128/774; 128/694; 128/721; 604/31; 604/50; 604/66
[58] Field of Search ..................... 128/677, 678, 128/679, 686, 694, 721, 774, 782; 604/30, 31, 50, 65, 66

[56] References Cited

U.S. PATENT DOCUMENTS

| | | | |
|---|---|---|---|
| 3,847,142 | 11/1974 | Williams et al. | 128/694 |
| 4,258,720 | 3/1981 | Flowers | 128/774 |
| 4,456,015 | 6/1984 | Sackner | 128/774 |
| 4,572,211 | 2/1986 | Sagalowsky | 128/774 |
| 4,703,678 | 11/1987 | Karacan et al. | 128/774 |
| 4,817,625 | 4/1989 | Miles | 128/721 |
| 4,846,462 | 7/1989 | Regnier et al. | 128/721 |
| 4,875,488 | 10/1989 | Shimazu et al. | 128/774 |
| 4,909,260 | 3/1990 | Salem et al. | 128/721 |
| 4,960,118 | 10/1990 | Pennock | 128/721 |

*Primary Examiner*—Max Hindenburg
*Attorney, Agent, or Firm*—R. Neil Sudol; Henry D. Coleman

[57] ABSTRACT

A medical method comprises the steps of attaching a sensing device to a limb of a patient, automatically operating the sensing device to monitor a circumference of the limb, automatically comparing a measured circumference with a reference value, and automatically generating an alarm signal upon detecting that the measured circumference differs from the reference value by more than a predetermined magnitude. In one application of the method, an intravenous catheter is inserted into a blood vessel in the limb, and a fluid is fed into the blood vessel via the catheter. The limb is covered upon insertion of the catheter and attachment of the sensing device, thereby preventing direct visual observation of the limb during performance of a surgical operation on the patient. The circumference measurements and automatic comparisons are performed periodically. In another application of the method, where the limb is one leg of the patient, a detecting device attached to the other leg of the patient, monitors a circumference of that other leg. The circumferences of the two legs are peridocially compared with one another and with reference values to determine an increase in circumference of just one leg, indicating possible phlebitis.

19 Claims, 3 Drawing Sheets

LIMB MONITORING METHOD AND ASSOCIATED APPARATUS

BACKGROUND OF THE INVENTION

This invention relates to a method and associated apparatus for detecting an abnormal medical condition of a patient's limb. More particularly, this invention pertains to a method and associated apparatus for monitoring limbs for the abnormal infusion of fluids into the limbs.

In certain kinds of thoracic surgery, e.g., open heart surgery, it is necessary to keep the arms of the patient extending alongside the patient's flanks. This arm configuration maximizes the number of surgical personnel who can stand beside the patient. At least one arm of the patient is infused with blood via an intravenous catheter. The arm and the catheter are covered with a drape sheet during the operation.

Because the patient is occasionally moved during surgery, the catheter can become displaced and can perforate the vein so that blood infiltrates the tissues of the arm rather than being fed into the cardiovascular system. Because the arm is covered, the infiltration is frequently not detected until the missing blood results in other symptoms. Infiltration can also result in a so-called compartment syndrome wherein the pressurized fluid in the muscular tissues collapses arteries feeding the arm and thereby prevents oxygenation of the tissues of the arm.

Clearly, infiltration represents a serious problem in thoracic surgery.

A different sort of problem in hospitals is phlebitis, particularly in the patients' legs. A need exists for a technique which will result in the early detection of phlebitis, before the condition becomes severe.

OBJECTS OF THE INVENTION

An object of the present invention is to provide a method and/or an associated apparatus for monitoring a limb of a patient to detect abnormal infusion of fluid into the limb.

Another, more particular, object of the present invention is to provide a method and/or an associated apparatus for detecting blood infiltration into a covered limb during a surgical operation.

Another particular object of the present invention is to provide a method and/or an associated apparatus for detecting the infusion of blood fluids into a patient's leg and, concomitantly, phlebitis in that leg.

These and other objects of the present invention will be apparent from the drawings and detailed descriptions herein.

SUMMARY OF THE INVENTION

A medical device comprises, in accordance with the present invention, a monitoring component for sensing a linear dimension of a body appendage, an attachment element supporting the monitoring component for attaching the monitoring component to the body appendage, and an alarm component operatively connected to the monitoring component for generating an alarm signal upon detecting an increase in the linear dimension of the body appendage greater than a predetermined amount.

The monitoring component may include a strain gauge mounted to the attachment element, which itself may take the form of a band or strip securable to the patient's appendage, e.g., via VELCRO type hook and loop fasteners or snap lock fasteners or an adhesive layer. The alarm component may include an auditory signal generator (electro-acoustic transducer) or a visual signal generator such as a light emitting diode.

According to another feature of the present invention, the alarm component includes a comparator operatively connected to the monitoring component for comparing a sensed linear dimension of the body appendage with a reference linear dimension. It is contemplated that the reference linear dimension is an initial linear dimension of the appendage and is measured and stored in encoded form in a memory of the device.

According to a further feature of the present invention, the medical device further comprises a sensor for measuring a linear dimension of a body limb different from the appendage. A fastener supports the sensor and serves to attach the sensor to the limb. The alarm component is also operatively connected to the sensor for generating an alarm signal upon detecting an increase in the linear dimension of the patient's body appendage relative to a linear dimension of the body limb. The alarm component may include another comparator operatively connected to the sensor for comparing a sensed linear dimension of the body appendage with a measured linear dimension of the body limb.

As discussed in greater detail hereinafter with reference to the method of the invention, the limb and the appendage of the patient may be the legs of the patient. In that event, the invention functions to detect leg swelling correlated with phlebitis.

A medical method for reducing risk of patient injury during a surgical operation comprises, in accordance with a specific embodiment of the present invention, the steps of (i) inserting an intravenous catheter into a blood vessel in a body limb of a patient, (ii) feeding a fluid into the blood vessel via the catheter, (iii) covering the limb, thereby preventing direct visual observation of the limb, (iv) performing a surgical operation on the patient, (v) automatically and periodically monitoring a linear dimension of the limb during the performance of the operation, and (vi) generating an alarm signal upon detecting an increase in the linear dimension greater than a predetermined threshold.

Pursuant to an additional feature of the present invention, this method further comprises the step of reinserting the catheter into a cardiovascular vessel in the limb upon generation of the alarm signal. The reinsertion may be into the same blood vessel as originally inserted, or a different vessel.

Pursuant to another feature of the present invention, the automatic monitoring of the limb linear dimension includes the step of sensing current in a strain gauge. The method then further comprises the step of attaching the strain gauge to the limb prior to covering the limb, e.g., with a drape sheet. The strain gauge may be attached directly to the limb, for example, via adhesive or mounted to a band which in turn is attached to the limb via VELCRO type hook and loop fasteners or snap lock fasteners or an adhesive layer.

Pursuant to a further feature of the present invention, the automatic monitoring of the limb linear dimension includes the step of automatically comparing a sensed linear dimension of the limb with a predetermined reference linear dimension. The reference linear dimension may be an initial linear dimension of the limb.

A medical method for detecting phlebitis in a leg of a patient comprises, in accordance with another conceptualization of the present invention, the steps of (a) automatically monitoring a first linear dimension of one leg of the patient, (b) automatically detecting a second linear dimension of another leg of the patient, (c) automatically comparing the first linear dimension with a reference value of the first linear dimension, (d) automatically comparing the second linear dimension with a reference value of the second linear dimension, (e) automatically comparing an increase in size of the first linear dimension with a change in size of the second linear dimension, and (f) automatically generating an alarm signal upon determining that the linear dimension of the one leg has increased by an amount greater than an increase in size of the other leg, thereby indicating the presence of phlebitis in the one leg.

Preferably, the monitoring and comparing steps are performed periodically.

In accordance with another feature of the present invention, the step of automatically comparing the first linear dimension with a reference value of the first linear dimension includes the step of calculating a first difference between the first linear dimension and its respective reference value. Similarly, the step of automatically comparing the second linear dimension with a reference value of the second linear dimension includes the step of calculating a second difference between the second linear dimension and its respective reference value, while the step of automatically comparing a detected increase in size of the first linear dimension with a detected change in size of the second linear dimension includes the steps of calculating a third difference between the first difference and the second difference and comparing the third difference with a pre-established reference value.

In accordance with a supplemental feature of the present invention, the steps of automatically monitoring and automatically detecting each include the step of sensing current in a respective strain gauge attached to the one leg and to the other leg prior to the steps of automatically monitoring and automatically detecting.

Preferably, the reference linear dimensions are initial linear dimensions of the respective legs.

A medical method comprises, in accordance with a more general conceptualization of the present invention, the steps of attaching a sensing device to a limb of a patient, automatically operating the sensing device to monitor a linear dimension of the limb, automatically comparing, with a reference value, a linear dimension of the limb measured during the step of operating, and automatically generating an alarm signal upon detecting, in the step of comparing, that the measured linear dimension differs from the reference value by more than a predetermined magnitude.

As discussed above, the method may further comprise the steps of inserting an intravenous catheter into a blood vessel in the limb, feeding a fluid into the blood vessel via the catheter, covering the limb upon insertion of the catheter and attachment of the sensing device, thereby preventing direct visual observation of the limb, and performing a surgical operation on the patient. The steps of operating the sensing device and comparing the measured linear dimension are periodically executed during the performing of the operation.

As additionally discussed hereinabove, where the limb is one leg of the patient, the method may alternatively comprise the further steps of attaching a detecting device to another leg of the patient, automatically operating the detecting device to monitor a linear dimension of the other leg, automatically comparing, with another reference value, a linear dimension of the other leg measured via the detecting device, and automatically comparing a measured increase in linear dimension of the one leg with a measured change in size of the other leg. In this embodiment of the invention, the step of generating an alarm signal is implemented upon determining that the linear dimension of the one leg has increased in size by an amount greater than the linear dimension of the other leg, thereby indicating the presence of phlebitis in the one leg.

The present invention provides a method and an associated apparatus which automatically monitors a limb of a patient to detect abnormal infusion of fluid into the limb. This is useful to prevent extensive infiltration of infused blood during thoracic surgery and to detect phlebitis in a leg of a hospitalized patient. In the former case, the limb linear dimension need be monitored for a matter of hours, whereas in the latter case, the monitoring extends over days, if not weeks or months.

DETAILED DESCRIPTION

Figure 1:
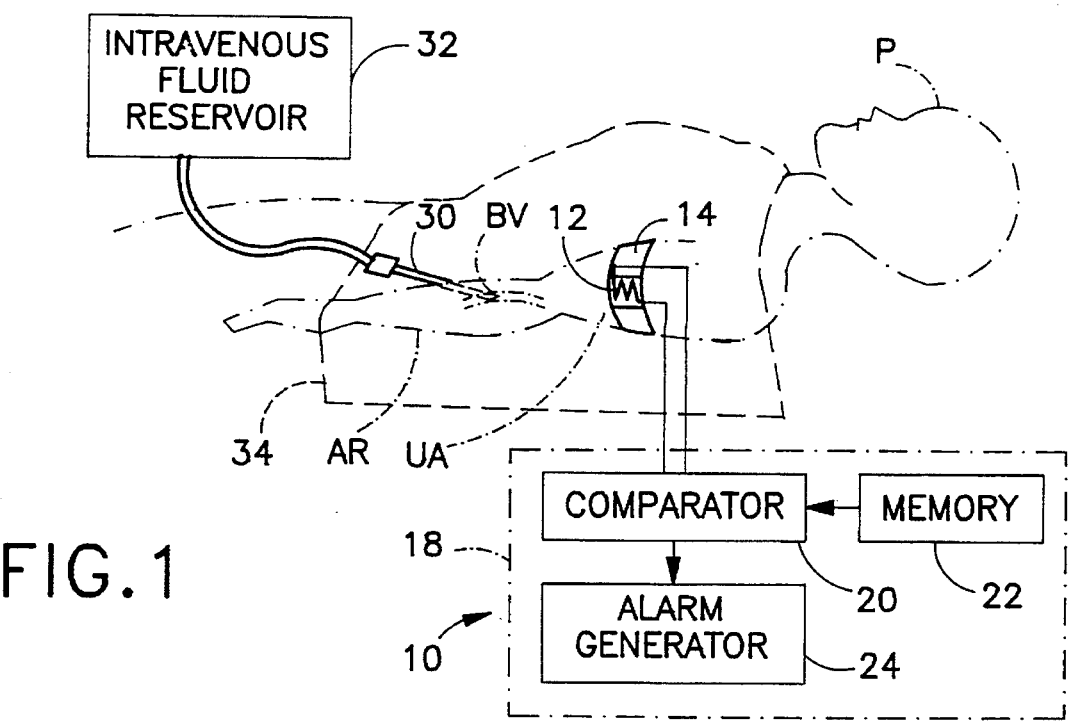
FIG. 1 is basically a block diagram of an apparatus in accordance with the present invention for detecting blood infiltration into a covered limb during a surgical operation.

As illustrated in FIG. 1, a medical device 10 comprises a sensor 12 in the form of a strain gauge for monitoring a circumference of a body appendage, particularly an upper arm UA of a patient P during a thoracic surgical procedure such as open heart surgery. Strain gauge sensor 12 is provided on an attachment element 14 in the form of a band or strap (see also FIG. 3) which is securable to the upper arm UA via an adhesive layer 16. Attachment element 14 may be provided with other, equivalent fasteners such as VELCRO type hook and loop fasteners or snap lock fasteners (neither illustrated).

An alarm or indicator component 18 is operatively connected to sensor 12 for generating an alarm signal upon detecting an increase in the circumference of arm UA which is greater than a predetermined amount. More specifically, alarm component 18 includes a comparison circuit 20 operatively connected to sensor 12 for comparing a sensed circumference of arm UA with a reference circumference stored in encoded form in a memory 22. The reference circumference is an initial circumference of upper arm UA and is measured prior to the start of the surgical operation.

Alarm component 18 further includes an alarm signal generator 24 which may take the specific form of an electroacoustic transducer 26 (FIG. 2) or a light emitting diode ("LED") 28.

Figure 2:
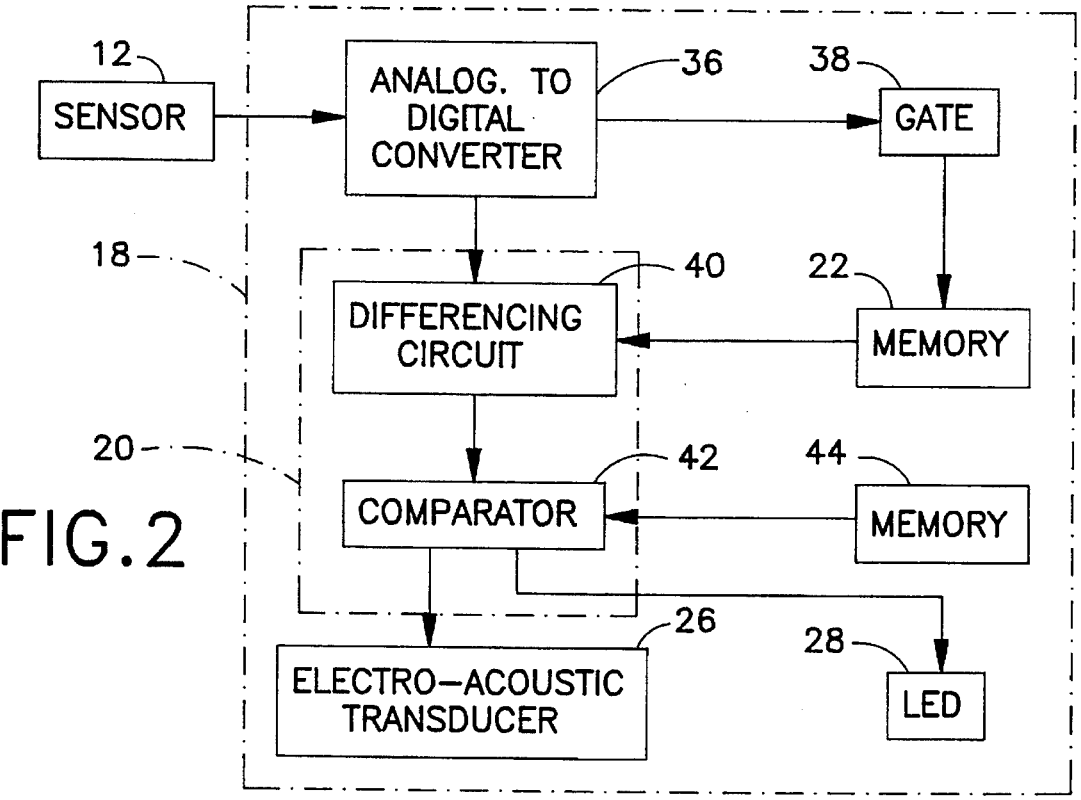
FIG. 2 is a block diagram showing detailed componentry of the apparatus of FIG. 1.
Figure 3:
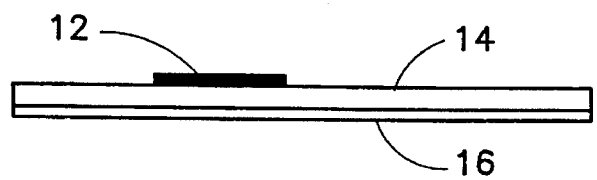
FIG. 3 is a schematic side elevational view of an attachment element for a sensor component of the apparatus of FIGS. 1 and 2.

The medical device of FIGS. 1–3 is used to automatically monitor the circumference of the upper arm during the surgical operation to determine whether a size increase has occurred due to infiltration of the arm's tissues. As illustrated diagrammatically in FIG. 1, an intravenous catheter 30 is inserted into a blood vessel BV in the patient's arm AR. During the surgical procedure, a fluid such as blood or plasma is fed from a reservoir 32 into blood vessel BV via catheter 30. Prior to the procedure, arm AR and upper arm UA are covered with a drape sheet 34, which prevents direct visual observation of the patient's arm. During the surgical procedure, the circumference of UA is automatically and peridoically monitored by operation of sensor 12. If comparison circuit 20 detects an increase in the circumference of upper arm UA greater than a predetermined threshold, the comparator induces generator 24 to produce an alarm signal.

The signal produced by alarm signal generator 24 alerts the surgeon(s) to possible infiltration of the intrvenous fluid into the tissues of arm AR and upper arm UA. Drape sheet 34 is then pulled away and catheter 30 reinserted, either in blood vessel BV or a different vein in arm AR.

The automatic monitoring of the circumference of upper arm UA is implemented in part by sensing current in strain gauge sensor 12. To that end, sensor 12 is connected to an analog-to-digital converter 36 (FIG. 3). A manually activatable gate 38 is connected at an input to converter 36 and at an output to memory 22, whereby an initial circumference is stored in memory 22 to serve as a reference value.

As further illustrated in FIG. 2, comparison circuit 20 includes an algebraic differencing circuit 40 which produces a signal encoding a difference between a measured circumference and the reference circumference stored in memory 22. That signal is fed to a comparator 42 which compares the difference value with a predetermined threshold stored in a memory or register 44. That threshold value serves to eliminate inconsequential variations in circumference which may arise, for example, from inadvertant pressure exerted on attachment element 14 by surgical personnel during a shifting of the patient.

It is to be noted that strain gauge sensor 12 may be attached directly to upper arm UA, for example, via adhesive. Also, memories 22 and 44 may be elements of the same solid state circuit.

Figure 4:
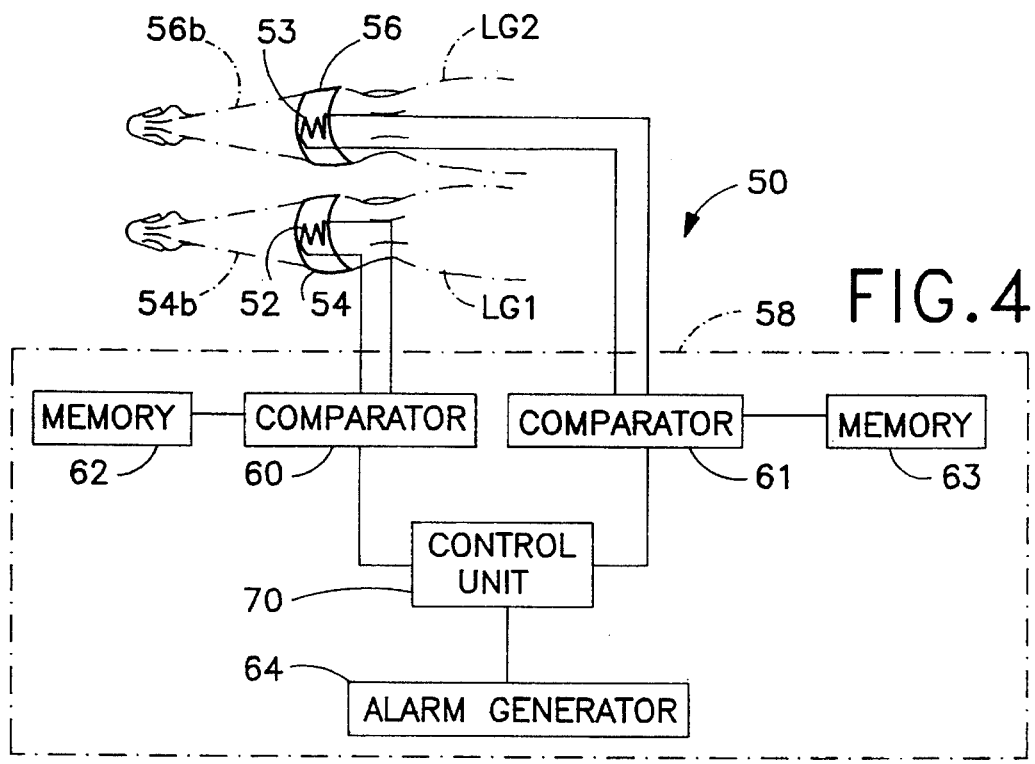
FIG. 4 is basically a block diagram of an apparatus in accordance with the present invention for detecting the infusion of blood fluids into a patient's leg and, concomitantly, phlebitis in that leg.

As illustrated in FIG. 4, another medical limb measuring device 50 comprises a pair of sensors 52 and 53 in the form of respective strain gauges for monitoring circumferences of a patient's legs LG1 and LG2 to detect an increase in size of one of the legs which is indicative or symptomatic of phlebitis.

Strain gauge sensors 52 and 53 are provided on respective attachment elements 54 and 56 which take the form of bands or straps securable to legs LG1 and LG2, e.g., via adhesive layers, hook and loop fasteners, etc. Alternatively or additionally, bands or strips 54 and 56 may be incorporated into medical compression type stockings 54b and 56b.

An alarm or indicator component 58 is operatively connected to sensors 52 and 53 for generating an alarm signal upon detecting an increase in the circumference of one leg LG1 or LG2 which has not occurred in the other leg LG2 or LG1. More specifically, alarm component 58 includes a pair of comparison circuits 60 and 61 operatively connected to sensors 52 and 53, respectively, for comparing sensed circumferences of legs LG1 and LG2 with respective reference circumferences stored in encoded form in memories 62 and 63. These reference circumferences are initial circumferences of legs LG1 and LG2 and are measured at the onset of a monitoring procedure.

Alarm component 58 further includes an alarm signal generator 64 which may take the specific form of an electroacoustic transducer 66 (FIG. 5) or a light emitting diode ("LED") 68. Alarm signal generator 64 is activated by a control unit 70 which receives signals from comparison circuits 60 and 61.

Figure 5:
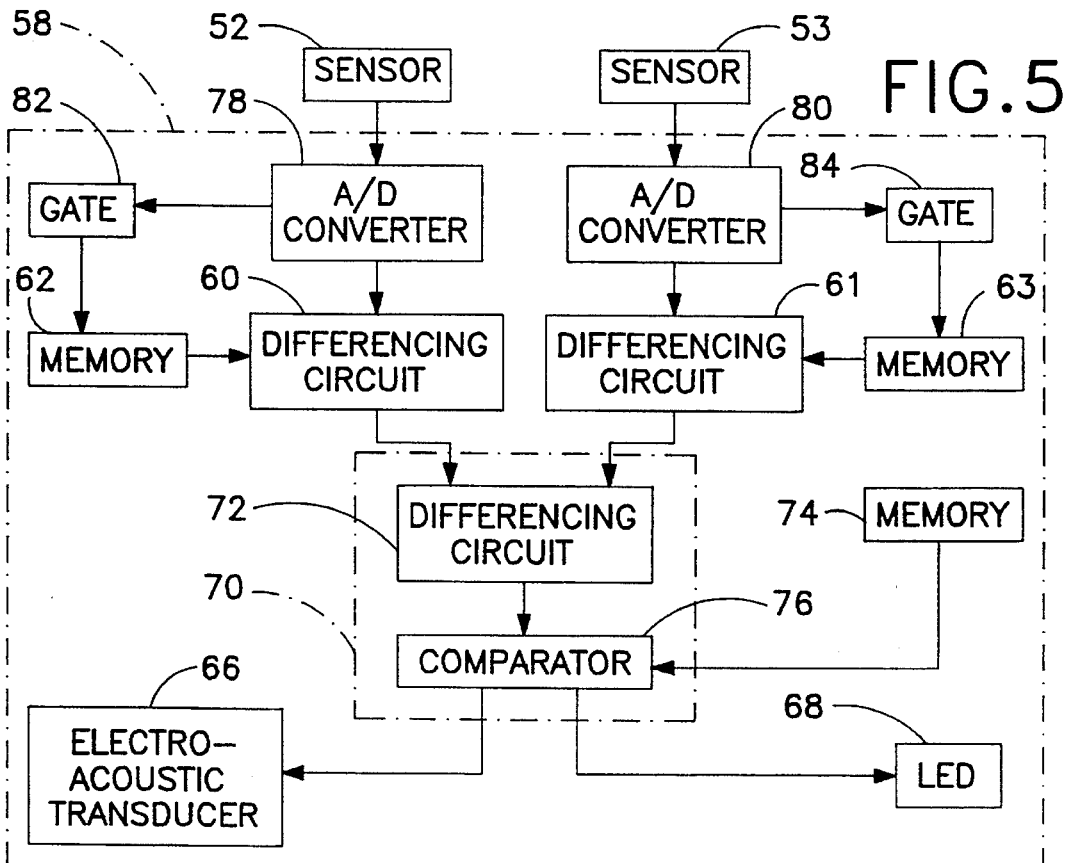
FIG. 5 is a block diagram showing detailed componentry of the apparatus of FIG. 4.

Sensors 52 and 53 serve to automatically monitor, detect or measure circumferences of legs LG1 and LG2. This monitoring occurs periodically. As illustrated in FIG. 5, comparators 60 and 61 may take the more particular form of differencing circuits which automatically calculate algebraic differences between the contemporaneous or real-time leg circumferences as measured by sensors 52 and 53 and the respective initial leg circumferences stored in encoded form in memories 62 and 63. Differencing circuits 60 and 61 are connected at outputs to a further differencing circuit 72 which is part of control unit 70. Circuit 72 computes the algebraic difference between the differences calculated by circuits 60 and 61 and in effect compares the measured circumferences of legs LG1 and LG2 to detect a change in circumference of one leg LG1 or LG2 with respect to the other leg LG2 or LG1. In other words, differencing circuit 72 automatically compares increases in leg circumference with one another to determine relative changes in leg size. If a detected relative change is greater than a predetermined reference value or magnitude which is stored in a memory 74, i.e., if the circumference of the one leg LG1 or LG2 has increased by an amount greater by a predetermined limit than an increase in size of the other leg LG2 or LG1, an alarm signal is generated. To that end, control unit 70 further includes a comparator 76 connected at inputs to differencing circuit 72 and memory 74 and at an output to electroacoustic transducer 66 and LED 68.

A change in leg size determined by control unit 70 functions to indicate the presence of phlebitis in the one leg.

Differencing circuits 60 and 61 receive digitally encoded leg circumference values from analog-to-digital (A/D) converters 78 and 80 which are connected at their inputs to sensors 52 and 53, respectively. Converters 78 and 80 are also connected via manually activatable gates 82 and 84 to memories 62 and 63 for loading leg circumference reference values into those storage components.

Comparator 76 may be configured to compare positive and negative reference values from memory 74 with a leg circumference difference determined essentially in real time by circuit 72, where both legs LG1 and LG2 are susceptible to phlebitis.

Figure 6:
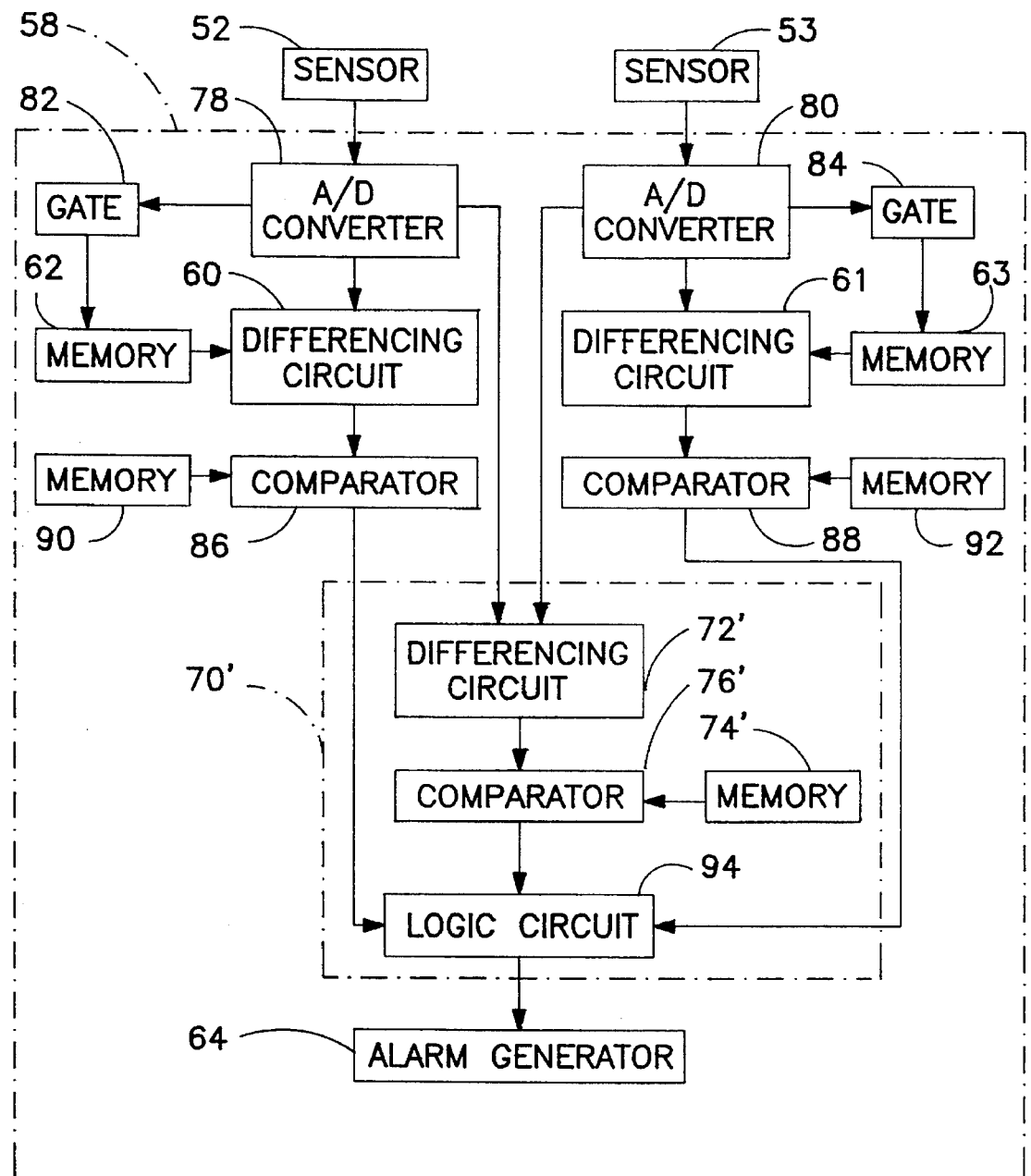
FIG. 6 is a block diagram showing alternative componentry of the apparatus of FIG. 4.

FIG. 6 illustrates a modified embodiment of the phlebitis detection device of FIG. 4. Like components in FIGS. 4, 5 and 6 are designated by like reference numerals. As depicted in FIG. 6, differencing circuits 60 and 61 are connected at their outputs to respective comparators 86 and 88 which compare the algebraic leg circumference differences from circuits 60 and 61 with respective pre-established limits or thresholds stored in memories 90 and 92. Where comparator 86 or 88 determines that the respective leg LG1 or LG2 has changed (increased, generally) in size by more than a predetermined limit or threshold, the comparator 86 or 88 generates a signal which is transmitted to a logic circuit 94 in a modified control unit 70'.

Modified control unit 70' also includes a differencing circuit 72' which is connected at its inputs to A/D converters 78 and 80 for receiving therefrom the real time or contemporaneous encoded leg circumferences measured by sensors 52 and 53. Circuit 72' computes the difference between the measured leg circumferences and transmits the difference to a comparator 76'. Comparator 76' compares the difference value with a threshold or limit value stored in a memory 74'.

If the difference value exceeds the threshold, then comparator 76' transmits a signal to logic circuit 94. Where logic circuit 94 receives a signal from comparator 76' and a signal from comparator 86 and/or comparator 88, an alarm is produced by generator 64.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that the circumference of a limb is a linear dimension, characterized by linear units. Accordingly, the instant invention can be realized, equivalently, by measuring another linear dimension such as limb diameter. Accordingly, it is to be understood that the drawings and descriptions herein are proffered by way of example to facilitate comprehension of the invention and should not be construed to limit the scope thereof.

What is claimed is:

1. A medical device for detecting phlebitis in a leg of a patient, comprising:

monitoring means for monitoring a first linear dimension of one leg of the patient;

detecting means for detecting a second linear dimension of another leg of the patient;

first comparing means operatively connected to said monitoring means for comparing said first linear dimension with a reference value of said first linear dimension;

second comparing means operatively connected to said detecting means for comparing said second linear dimension with a reference value of said second linear dimension;

third comparing means operatively connected to said first comparing means and said second comparing means for comparing an increase in size of said first linear dimension with a change in size of said second linear dimension; and alarm generating means operatively connected to said third comparing means for generating an alarm signal upon determining that said first linear dimension has increased by an amount greater than an increase in size of said another leg, thereby indicating the presence of phlebitis in said one leg.

2. The device defined in claim 1 wherein said monitoring means includes a strain gauge mounted to said attachment means.

3. The device defined in claim 1 wherein said alarm generating means includes an auditory signal generator.

4. A medical method for reducing risk of patient injury during a surgical operation, comprising the steps of:

inserting an intravenous catheter into a blood vessel in a body limb of a patient;

feeding a fluid into said blood vessel via said catheter;

covering said limb, thereby preventing direct visual observation of said limb;

performing a surgical operation on the patient;

during said step of performing, automatically and periodically monitoring a linear dimension of said limb; and upon detecting an increase in said linear dimension greater than a predetermined threshold, generating an alarm signal.

5. The method defined in claim 4, further comprising the step of reinserting said catheter into a cardiovascular vessel in said limb upon generation of said alarm signal.

6. The device defined in claim 5 wherein said cardiovascular vessel is said blood vessel.

7. The method defined in claim 4 wherein said step of automatically monitoring includes the step of sensing current in a strain gauge, further comprising the step of attaching said strain gauge to said limb prior to said step of covering.

8. The method defined in claim 4 wherein said step of automatically monitoring includes the step automatically comparing a sensed linear dimension of said limb with a predetermined reference linear dimension.

9. The method defined in claim 8 wherein said reference linear dimension is an initial linear dimension of said limb.

10. The method defined in claim 4 wherein said step of performing includes the performance of open heart surgery.

11. A medical method for detecting phlebitis in a leg of a patient, comprising the steps of:

(a) automatically monitoring a first linear dimension of one leg of the patient;

(b) automatically detecting a second linear dimension of another leg of the patient;

(c) automatically comparing said first linear dimension with a reference value of said first linear dimension;

(d) automatically comparing said second linear dimension with a reference value of said second linear dimension;

(e) automatically comparing an increase in size of said first linear dimension with a change in size of said second linear dimension; and (f) automatically generating an alarm signal upon determining that said first linear dimension has increased by an amount greater than an increase in size of said another leg, thereby indicating the presence of phlebitis in said one leg.

12. The method defined in claim 11 wherein said steps (a) through (e) are performed periodically.

13. The method defined in claim 11 wherein said step (c) includes the step of calculating a first difference between said first linear dimension and its respective reference value, said step (d) includes the step of calculating a second difference between said second linear dimension and its respective reference value, and said step (e) includes the steps of calculating a third difference between said first difference and said second difference and comparing said third difference with a pre-established reference value.

14. The method defined in claim 11 wherein said steps of automatically monitoring and automatically detecting each include the step of sensing current in a respective strain gauge attached to said one leg and to said another leg prior to said steps of automatically monitoring and automatically detecting.

15. The method defined in claim 11 wherein said reference linear dimensions are initial linear dimensions of the respective legs.

16. A medical method comprising the steps of:

attaching a sensing device to a limb of a patient;

automatically operating said sensing device to monitor a linear dimension of said limb;

inserting an intravenous catheter into a blood vessel in said limb;

feeding a fluid into said blood vessel via said catheter;

upon completion of said steps of attaching and inserting, covering said limb, thereby preventing direct visual observation of said limb;

automatically comparing, with a reference value, a linear dimension of said limb measured during said step of operating;

performing a surgical operation on the patient, the operating of said sensing device and the comparing of said linear dimension with said reference value being periodically executed during the performing of said surgical operation; and automatically generating an alarm signal upon detecting, in said step of comparing, that the measured linear dimension differs from said reference value by more than a predetermined magnitude.

17. The method defined in claim 16 wherein said sensing device includes a strain gauge, said step of operating said sensing device including the step of sensing current in said strain gauge.

18. The method defined in claim 16 wherein said reference linear dimension is an initial linear dimension of said limb, further comprising the step of storing said initial linear dimension in a memory.

19. The method defined in claim 16 wherein said limb is one leg of the patient, further comprising the steps of:

attaching a detecting device to another leg of the patient;

automatically operating said detecting device to monitor a linear dimension of said another leg;

automatically comparing, with another reference value, a linear dimension of said another leg measured via said detecting device; and automatically comparing a measured increase in linear dimension of said one leg with a measured change in size of said another leg, said step of generating an alarm signal being implemented upon determining that the linear dimension of said one leg has increased in size by an amount greater than the linear dimension of said another leg, thereby indicating the presence of phlebitis in said one leg.

* * * * *